(12) United States Patent
Mereyala et al.

(10) Patent No.: US 6,933,382 B2
(45) Date of Patent: Aug. 23, 2005

(54) PROCESS FOR THE SYNTHESIS OF 2-DEOXY-D-GLUCOSE

(75) Inventors: Hari Babu Mereyala, Andhra Pradesh (IN); Mamidyala Sreeman Kumar, Andhra Pradessh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/392,396

(22) Filed: Mar. 20, 2003

(65) Prior Publication Data

US 2004/0185538 A1 Sep. 23, 2004

(51) Int. Cl.$^7$ .............................. C07H 1/00; C13K 1/00
(52) U.S. Cl. .......................................... 536/124; 127/36
(58) Field of Search .............................. 536/124; 127/36

(56) References Cited

U.S. PATENT DOCUMENTS 6,319,695 B1 * 11/2001 Wong et al. .................. 435/97

OTHER PUBLICATIONS

Boivin et al., "Synthese D'UN Disaccharide, Constituant Naturel D'Anthracyclines Antibiotiques Et Antitumorales" Tetrahedron Letters, Elsevier Science Publishers, Amsterdam, NL, vol. 21, No. 25, 1980, pp. 2413–2416, (abstract only).

Binkley et al., "Photochemically based Synthesis of Deoxy Sugars, Synthesis of 2–deoxy–D–arabino–hexopyranose (2–deoxy–D–glucose) and several of its derivatives from 3,4,6,–tri–O–acetyl–D–glucal", Journal of Carbohydrate Chemistry (1982), 1(1), 1–8.

Monneret, et al., "A Convenient Synthesis of 2–deoxy–D–arabino–hexose and of its methyl and benzyl glycosides", Carbohydrate Research, vol. 96, 1981, pp. 299–305, XP009009800.

Marzabadi et al., "The Chemistry of Glucal Halohydrins: The Effect of the Halide on Epoxide Formation", Tetrahedron, Elsevier Science Publishers, Amsterdam, NL, vol. 50. No. 23, 1994, pp. 6783–6796, XP001147278.

Kottenhahn et al., "Synthese Von 2–Desoxy–Alpha–O–Glycopeptiden Mit Dem N–Ioduccinimid–(NIS)– Verfahren Synthesis of 2–Deoxy–Alpha–O–Glycopeptides by the N–Iodosuccinimide (NIS) Procedure" Liebigs Annalen der Chemie, Verlag Chemie GMBH, Weinheim, DE, No. 8, 1991, pp. 727–744, XP001147767, (abstract only).

Wëssel et al., "The Synthesis of the 2– and 2'–monodeoxygenated Analogues of Beta–Maltosyl–(1 4) Trehalose" Journal of Carbohydrate Chemistry, New York, NY, US., vol. 17, No. 4/5, May 1998, pp. 567–586, XP009009837.

Costantino et al., "A Mild and Easy One–pot Procedure for the Synthesis of 2–deoxysugars from glycals", Tetrahedron Letters, Elsevier Science Publishers, Amsterdam, NL, vol. 41, No. 47, Nov. 18, 2000, pp. 9177–9180, XP004236212.

Overend et al., "Deoxy–sugars. Part VII. A Study of the Reactions of Some Derivatives of 2–deoxy–D–glucose", Journal of the Chemical Society, 1949, pp. 2841–2845.

Friesen, R.W., et al., "On the Controlled Oxidative Coupling of Glycals: A New Strategy for the Rapid Assembly of Oligosaccharides," J. Am. Chem. Soc., vol. 111, No. 17, 1989, pp. 6656–6660.

* cited by examiner

Primary Examiner—James O. Wilson
Assistant Examiner—Everett White
(74) Attorney, Agent, or Firm—Nixon & Vanderhye P.C.

(57) ABSTRACT

The present invention provides a process for the synthesis of 2-deoxy-D-glucose comprising haloalkoxylation of R-D-Glucal wherein R is selected from H and 3, 4, 6-tri-O-benzyl, to obtain alkyl 2-deoxy-2-halo-R-α/β-D-gluco/mannopyranoside, converting alkyl 2-deoxy-2-halo-R-α/β-D-gluco/mannopyranoside by reduction to alkyl 2-deoxy-α/β-D-glucopyranoside, hydrolysing alkyl 2-deoxy-α/β-D-glucopyranoside to 2-deoxy-D-glucose.

27 Claims, No Drawings

PROCESS FOR THE SYNTHESIS OF 2-DEOXY-D-GLUCOSE

FIELD OF THE INVENTION

The present invention relates to a process for the synthesis of 2-deoxy-D-glucose.

BACKGROUND OF THE INVENTION 2-deoxy-D-glucose is useful in control of respiratory infections and for application as an antiviral agent for treatment of human genital herpes.

Prior art for preparation of 2-deoxy-D-glucose while operable, tend to be expensive and time consuming. Reference may be made to Bergmann M., Schotte, H., Lechinsky, W., Ber, 55, 158 (1922) and Bergmann, M., Schotte, H., Lechinsky, W., Ber 56, 1052 (1923) which disclose the preparation of 2-deoxy-D-glucose in low yield by mineral acid catalyzed addition of water to D-glucal. Another method of producing 2-deoxy-D-glucose is from diethyldithioacetal derivative of D-glucose (Bolliger, H. R. Schmid, M. D., *Helv. Chim. Acta* 34, 989 (1951); Bolliger, H. R., Schmid, M. D., *Helv; Chim. Acta* 34, 1597 (1951); Bolliger, H. R Schmid, M. D., *Helv. Chim. Acta* 34, 1671 (1951) and from D-arabinose by reaction with nitromethane followed by acetylation, reduction and hydrolysis (Sowden, J. C., Fisher, H. O. L., *J. Am. Chem.,* 69, 1048 (1947). However these methods result in the formation of 2-deoxy-D-glucose in low yield and of inferior purity due to the formation of several by-products and involve use of toxic reagents such as ethanethiol and nitromethane. As a result purification of 2-deoxy-D-glucose has to be done by recrystallisation which is tedious, time consuming and difficult.

Accordingly it is important to develop a process for synthesis of 2-deoxy-D-glucose which obviates the drawbacks as detailed above and results in good yield and good purity.

OBJECTS OF THE INVENTION

The main object of the present invention is to provide a process for the synthesis of 2-deoxy-D-glucose resulting in good yield and with good purity.

Another object of the invention is to provide an economical process for the synthesis of 2-deoxy-D-glucose.

SUMMARY OF THE INVENTION

A process that would produce 2-deoxy-D-glucose economically and with desired purity, is a welcome contribution to the art. This invention fulfills this need efficiently.

Accordingly the present invention relates to a process for the synthesis of 2-deoxy-D-glucose comprising haloalkoxylation of R-D-glucal wherein R is selected from H and 3,4,6-tri-O-benzyl, to obtain alkyl 2-deoxy-2-halo-R-α/β-D-gluco/mannopyranoside, converting alkyl 2-deoxy-2-halo-R-α/β-D-gluco/mannopyranoside by reduction to alkyl 2-deoxy-α/β-D-glucopyranoside, hydrolysing alkyl 2-deoxy-α/β-D-glucopyranoside to 2-deoxy-D-glucose.

In one embodiment of the invention, the alkyl 2-deoxy-α/β-D-glucopyranoside is obtained by
(a) haloalkoxylating 3,4,6, tri-O-benzyl-D-glucal to alkyl 2-deoxy-2-halo-3,4,6-tri-O-benzyl-α/β-D-gluco-/mannopyranoside,
(b) subjecting alkyl 2-deoxy-2-halo-3,4,6-tri-O-benzyl-α/β-D-gluco/mannopyranoside to reductive dehalogenation and debenzylation to obtain alkyl 2-deoxy-α/β-D-glucopyranoside.

In another embodiment of the invention, in step (a) haloalkoxylation of 3,4,6-tri-O-benzyl-D-glucal is carried out by reaction with a haloalkoxylating agent selected from a N-halosuccinimide and a N-haloacetamide, and alcohol.

In another embodiment of the invention, the N-halosuccinimide is selected from N-chloro- and N-bromosuccinimide.

In another embodiment of the invention, haloalkoxylation is carried out at a temperature in the range of 0° C.–30° C.

In another embodiment of the invention, the temperature is in the range of 5–10° C.

In another embodiment of the invention, the alcohol is selected from the group consisting of methanol, ethanol and isopropyl alcohol.

In another embodiment of the invention, the alcohol comprises stoichiometric amounts of alcohol contained in ethylene dichloride or dichloromethane.

In another embodiment of the invention, the N-haloacetamide is N-bromacetamide.

In another embodiment of the invention, step (b) is carried out in the presence of an alcohol selected from ethanol and isopropyl alcohol or water and in the presence of a scavenger selected from triethyl amine, $Na_2CO_3$, disopropyl amine and hexylamine.

In another embodiment of the invention, alkyl 2-deoxy-α/β-D-glucopyranoside is obtained by
(a) haloalkoxylating D-glucal to alkyl 2-deoxy-2-halo-α/β-D-gluco/mannopyranoside;
(b) subjecting alkyl 2-deoxy-2-halo-α/β-D-gluco/mannopyranoside to reductive dehalogenation and hydrogenation to obtain alkyl 2-deoxy-α/β-D-glucopyranoside.

In another embodiment of the invention, haloalkoxylation of D-glucal in step (a) comprises reaction with an haloalkoxylating agent selected from N-halosuccinimide and N-haloacetamide, and an alcohol.

In another embodiment of the invention, the N-halosuccinimide is selected from N-chloro- and N-bromosuccinimide.

In another embodiment of the invention, the haloalkoxylation is carried out in the presence of a solvent selected from the group consisting of EtOH, iPrOH, N,N-dimethyl formamide and stoichiometric amounts of alcohol.

In another embodiment of the invention, the reductive dehalogenation is carried out in the presence of a solvent selected from the group consisting of water, MeOH, EtOH and iPrOH, and with Pd/C 10% catalyst.

In another embodiment of the invention, the haloalkoxylation is bromomethoxylation, N-halosuccinimide is N-bromosuccinimide, alcohol is methanol and alkyl 2-deoxy-2-halo-α/β-D-gluco/mannopyranoside is methyl 2-bromo-2-deoxy-α/β-D-gluco/mannopyranoside.

In another embodiment of the invention, the hydrogenation is carried out at a pressure in the range of about 40–120 psi and in the presence of Raney-nickel catalyst, preferably in the form of a methanolic slurry.

In another embodiment of the invention, reductive dehalogenation is reductive debromination and said methyl 2-deoxy-2-halo-α/β-D-gluco-/mannopyranoside is methyl 2-bromo-2-deoxy α/β-D-gluco-/mannopyranoside and wherein the methyl 2-bromo-2-deoxy-α/β-D-gluco/mannopyranoside is converted to methyl 2-deoxy-α/β-D-glucopyranoside by hydrogenation using triethylamine at a pressure in the range of 40–120 psi in the presence of a Raney nickel catalyst.

In another embodiment of the invention, the alkyl 2-deoxy-α/β-D-glucopyranoside is directly hydrolysed to 2-deoxy-D-glucose by a hydrolysing agent selected from the group consisting of CF₃CO₂H, HCl and HOAc.

In another embodiment of the invention, hydrolysis of alkyl 2-deoxy-α/β-D-glucopyranoside to 2-deoxy-D-glucose is done at a temperature in the range of 20–90° C., In another embodiment of the invention, the alkyl 2-deoxy-α/β-D-glucopyranoside is first acetylated to alkyl 2-deoxy-3,4,6-tri-O-acetyl-α/β-D glucopyranoside which is then converted to 2-deoxy-1,3,4,6-tetra-O-acetyl-α/β-D-glucopyranoside which is then hydrolysed to 2-deoxy-D-glucose.

In another embodiment of the invention, the hydrolysis of 2-deoxy-1,3,4,6-tetra-O-acetyl-α/β-D-glucopyranoside comprises acid catalysed hydrolysis.

In another embodiment of the invention, the hydrolysis of 2-deoxy-1,3,4,6-tetra-O-acetyl-α/β-D-glucopyranoside comprises base catalysed hydrolysis.

In another embodiment of the Invention, the acid catalysed hydrolysis is carried out using a hydrolysing agent selected from the group consisting of aq. acetyl bromide, aq. acetyl chloride and aq. acetic acid.

In another embodiment of the invention, the base catalysed hydrolysis is carried out using a hydrolysing agent selected from the group consisting of NaOMe, NaOi-Pr, LiOMe, NaOBu, NH₃/MeOH. Bu₂SnO/MeOH.

In another embodiment of the invention, the alkyl is selected from the group consisting of methyl, ethyl and isopropyl.

DETAILED DESCRIPTION OF THE INVENTION

The preferred synthetic reactions and conditions for each individual steps of the above process are set forth below.

The reaction scheme for the reactions involved in the process of the invention are also given below:

N-chloroacetamide, N-bromoacetamide and alcohols such as methanol ethanol and propan-2-ol as reagents, Converting alkyl 2-deoxy-2-halo-3,4,6-tri-O-benzyl-α/β-D-gluco/mannopyrano-side (II) to alkyl 2-deoxy-α/β-D glucopyrannoside (III).

In effecting this conversion the preferred procedure is set forth in Lemieux et al, Can. J. Chem., 42,532 (1964) for analogous alkyl 2-bromo-2-deoxy-3,4,6,tri-O-acetyl-α/β-D-gluco/mannopyranoside. In this procedure alkyl 2-deoxy-2-halo-3,4,6-tri-O-benzyl-α/β-D-gluco/mannopyranoside is subjected to hydrogenation with 5% Pd/C at 40–200 psi pressure.

Converting D-glucal (IV) to alkyl 2-deoxy-2-halo-α/β-D-gluco-/mannopyranoside (V):

In effecting this conversion D-glucal is subjected to reaction conditions described by Lemieux et al, Can. J. Chem., 42,532 (1964) for analogous triacetyl D-glucal. Suitable haloalkoxylation reactions comprise using N-chlorosuccinimide, N-bromosuccinimide, N-chloroacetamide, N-bromoacetamide as haloalkoxylating agents and alcohols such as methanol, ethanol and propan-2-ol and the like as reagents.

Converting alkyl 2-deoxy-2-halo-α/β-D-gluco-/mannopyranoside (V) to alkyl 2-deoxy-α/β-D-glucopyranosides (III).

The procedure for effecting this conversions are set forth by Lemieux et al, Can J. Chem., 42,532 (1964) for analogous triacetyl derivative. In general this procedure involves hydrogenation of alkyl 2-bromo-2-deoxy-3,4,6-tri-O-acetyl-α/β-D-gluco/mannopyranoside with 5% Pd/C The standard method for effecting reductions in cases of this type also involves refluxing the halogen containing reactant with tri-alkyltinhydrides such as tributyltin hydride usually in aromatic solvents such as benzene, toluene or xylene containing catalytic amount of aza-bis-isobutyronitrile AIBN).

It is definitely preferable to employ a reduction process in which the alkyl 2-halo-2-deoxy-D-gluco-/mannopyranoside is hydrogenated at modest elevated pressure (40–120 psi) in

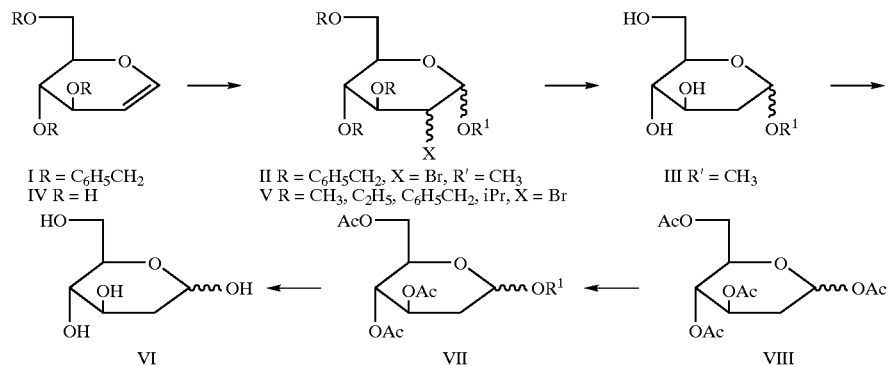

Such overall synthesis may be depicted as follows where R=H, CH₃, CH₂H₅, (CH₃)₂CH, C₆H₅CH₂; R¹—CH₃; X—CL, Br Converting 3,4,6-tri-O-benzyl-D-glucal (I) to alkyl 2-deoxy-2-halo-3,4,6-tri-O-benzyl-α/β-D-gluco-/mannopyranoside (II).

In effecting this conversion 3,4,6-tri-O-benzyl-D-glucal is subjected to reaction conditions described by Lemieux et al, Can. J. Chem, 42,532 (1964) for analogous acetyl derivative. Suitable haloalkoxylation reaction included N-chlorosuccinimide, N-bromosuccinimide, presence of a slurry of Raney-nickel in methanol and a suitable base such as trialkyl amine. Yields are high and pure product can be produced.

Converting alkyl 2-deoxy-α/β-D-glucopyranoside (III) to 2-deoxy-D-glucose (VI).

To produce 2-deoxy-D-glucose the alkyl 2-deoxy-α/β-D-glucopyranoside is subjected to acid catalysed hydrolysis for example by using acetic acid, hydrochloric acid, sulphuric acid, IR 120H+ resin, acetyl(chloride, acetyl bromide, benzoyl chloride or the like. The procedures for effecting such hydrolysis are standard and well known in the art. Converting alkyl 2-deoxy-3,4,6-tri-O-acetyl-α/β-D- glucopyranoside (VII) to 2-deoxy-1,3,4,6-tetra-O-acetyl-α/β-D-glucopyranoside (VIII)

In effecting this conversion the alkyl 2-deoxy-3,4,6-tri-O-acetyl-α/β-D-glucopyranoside was subjected to acetolysis with acetic acid/acetic anhydride/conc. sulphuric acid at 0° C.

Converting 2-deoxy-1,3,4,6-tetra-O-acetyl-α/β-D-glucopyranaoside (VIII) to 2-deoxy glucose (VI).

In effecting this conversion, 2-deoxy-1,3,4,6-tetra-O-acetyl-α/β-D-glucopyranoside was subjected to acid catalysed hydrolysis for example by using aq. Acetic acid, hydrochloric acid, sulphuric acid, acetyl chloride or the like.

Novelty and inventive steps of the present invention with respect to the prior art are—the present art doe not involve the use of toxic mercaptans like ethane thiol and this process does not involve reaction of D-glucal with mineral acid and hence avoids the formation of Ferrier by products.

The following examples are given by way of illustration and therefore should not be construed to limit the scope of the present invention

EXAMPLE 1

To a solution of 3,4,6-tri-O-benzyl-D-glucal (39 g, 0.09 mmol) in dichloromethane (20 ml) and methanol (100 ml) was added N-bromosuccinimide (18.7 g, 0.09 mil) during 10 min. at room temperature and stirred for 4 h. After completion of the reaction solvent was distilled off. The resultant residue extracted into carbon tetrachloride (2×100 ml) and organic phase concentrated to obtain methyl 2-bromo 2-deoxy-3,4,6-tri-O-benzyl-α/β-D-gluco-/mannopyranoside as a syrup. Quantity obtained 50 g. $^1$H NMR (200 MHz, CDCl$_3$) 3.40–4.00 (m, 7H, H-2,5,6,6' and OCH$_3$) 4.30–5.10 (m, 9H, H-1,3,4 and 3×PhCH$_2$O), 7.10–7.60 (m 15H, Ar—H). A solution of methyl 2-bromo-2-deoxy-3,4,6-tri-O-benzyl/α/β-D-gluco-/mannopyranoside (50 g) in methanol (300) was charged into one liter autoclave along with Raney nickel (10 ml) Et$_3$N (135 ml) and subjected to hydrogenation at 120 psi pressure at 50° C. for 8 h. After completion of the reaction the catalyst was filtered off and the residue washed with methanol (25 ml). The filtrate was concentrate to obtain methyl 2-deoxy-3,4,6-tri-O-benzyl-α/β-D-glucopyranoside as a syrup (37.9 g, 89%). $^1$H NMR (200 MHz CDCl$_3$): δ 1.50–2.40 (m,2H,H-2,2'), 3.32, 3.51 (2s, 3H, OCH$_3$) 3.55–4.00 (m, 5, H-3,4,5,6,6') 4.30–5.00 (M 7H, 3×PhCH$_2$, H-1), 7.10–7.45 (m, 15H, Ar—H). The syrup of methyl 2-deoxy-3,4, 6-tri-O-benzyl-α/β-D-glucopyranoside (37.9 g) was dissolved in methanol (200 ml). 1 g of 5% Pd/C was added and hydrogenated at 150 psi pressure at room temperature. After 5 hours catalyst was filtered off and solvent evaporated. Quantity of the methyl 2-deoxy-α/β-D-glucopyranoside obtained 10.5 g (70%). [α]$_D$+25.7° (c 1.0, MeOH), $^1$H NMR (200 MHz, D$_2$O); δ 1.45–2.40 (m, 2H, H-2,2') 3.20–4.80, (m 9H, H-1,3,4,5,6,6'—OCH$_3$).

EXAMPLE 2

To a solution of D-glucal (64.6 g, 0.44 mmol) in methanol (325 ml) at 10° C. was added N-bromosuccinimide (78.7 g, 0.44 mol) during 40 min. maintaining the temperature between 10–15° C. during the addition. The reaction mixture was stirred at room temperature. After 5 hours solvent was evaporated to obtain a residue which was refluxed in ethyl acetate (100 ml). Ethyl acetate layer was discarded to leave a residue of methyl 2-bromo-2-deoxy-α/β-D-gluco/mannopyranoside (105 g) as a syrup. [α]$_D$+36° (c 1.0, MeOH). $^1$H NMR (200 MHz, D$_2$O): δ 3.47, 3.67 (2s, 3H, OCH$_3$), 3.70–4.05 (m, 6h, H-2,3,4,5,6,6'), 4.48–5.13 (2$_s$, 1H, 1H, H-1). The syrupy methyl 2-bromo-2-deoxy-α/β-D-gluco-/mannopyranoside was dissolved in methanol (400 ml), a slurry of 80 g Raney nickel (a 50% slurry in methanol), Et$_3$N (30 ml) and hydrogenated in a Parr apparatus at 120 psi. After 8–9 hours, the reaction mixture was filtered through a Celite filter pad and washed with MeOH. The washings and filtrate were combined and triturated with hexane to separate and remove by filtration insoluble triethylamine hydrobromide and traces of succinimide. The filtrate was concentrated to a residue. The isolated yield of methyl 2-deoxy-α/β-D-glucopyranoside was 89%.

Ethyl 2-bromo-2deoxy-α/β-D-gluco-/mannopyranoside:

When solvent was ethanol instead of methanol the compound obtained was ethyl 2-bromo-2deoxy-α/β-D-gluco-/mannopyranoside. $^1$H NMR (200 MHz, D$_2$O): δ 1.10–1.32 (m, 3H, CH$_3$), 2.80 (s, 4H, —CO(CH$_2$)$_2$CO—NH—), 3.40–4.10 (m, 8H, H-2,3,4,5,6,6', CH$_2$), 4.40, 5.20 (2s 1H, H-1, α/β).

Isopropyl 2-bromo-2-deoxy-α/β-D-gluco-/mannopyranoside:

When isopropanol instead of methanol was used as a solvent the compound obtained was isopropyl 2-bromo-2-deoxy-α/β-D-gluco/mannopyranoside, $^1$H NMR (200 MHz, D$_2$O): δ 1.10–1.30 (m, 6H, 2×CH$_3$) 2.80 (s, 4H, —CO(CH$_2$)$_2$CO—NH—), 3.60–4.60 (m 8H,H-2,3, 4,5,6,6', CH$_2$) 4.40, 5,30 (2s, 1H, H-1, α/β.

EXAMPLE 3

A mixture of D-glucal (64.6 g), methanol (400 ml), N-bromosuccinimide (79 g) were stirred at 15° C. for 6 h. The reaction mixture was hydrogenated in a Parr apparatus in presence of 60 g of Raney nickel catalyst (a 50% slurry in methanol) and triethylamine (62 ml). After 8–9 h, the reaction mixture was filtered on a Celite filter pad. The Celite pad was washed with methanol. The washings and filtrate were combined, concentrated to a thick heavy syrup, dissolve in chloroform (500 ml), pyridine (400 ml) and acetic anhydride (251 ml) was added while stirring, maintaining the temperature between 5–10° C. After 12 hours, the reaction mixture was diluted with CHCl$_3$ (500 ml) transferred to a separating funnel and organic phase was washed with water. The organic phase was separated, dried (Na$_2$SO$_4$) and concentrated to obtain methyl 2-deoxy-3,4, 6-tri-O-acetyl-2 deoxy-α/β-D-glucopyranoside as a syrup (163.43 g, 87%). [α]$_D$+65.0° (c 1.0, CHCl$_3$) $^1$H NMR (200 MHz, CDCl$_3$): δ 1.55–1.90 (m, 2H, H-22'), 2.01, 2.04, 2.11, 2.15, (4s, 9H, 3×OCOCH$_3$), 2.18, 3.40 (2s, 3H, OCH$_3$), 3.45–50 (m, 3H, H-5, 6,6') 4.80–5.40 (m, 3H,H-1,3,4). The syrup was dissolved in methanol (600 ml) 1N NaOMe in methanol (25 ml) was added and left at room temperature. After 6–10 h, dry CO$_2$ gas was passed into the reaction mixture, solvent was evaporated to obtain a syrupy residue. The residue was once again extracted into dry methanol and concentrated to obtain methyl 2-deoxy-α/β-D-glucopyranoside as syrup. Quantity obtained 81 g (92%).

EXAMPLE 4

A 500 ml round bottom flask equipped with magnetic stir bar was charged with a solution of D-glucal (323 g) in methanol (175 ml), cooled to 15° C., N-bromosuccinimide (NIBS) (39.4 g) was added and stirred or 6 hours at 15° C., The reaction mixture was concentrated to half the volume, cooled to 0° C. and separated succinimide, was removed by filtration. To the filtrate was added a slurry of 30 g Raney nickel (a 50% slurry in Methanol) Et$_3$N (32 ml) and hydrogenated in a Parr apparatus at 120 psi. After 7–8 hours, the reaction mixture was filtered through a Celite filter pad, and washed with MeOH. The washings and filtrate were combined and triturate with hexane to separate and remove by filtration insoluble triethylamine hydrobromide and succinimide. The filtrate was concentrated to a residue, dissolved in methanol and triturated with hexane to remove most of the triethylamine hydrobromide and succinimide. The filtrate was concentrated to obtain methyl 2-deoxy-α/β-D-glucopyranoside (85%).

EXAMPLE 5

To a stirred solution of methyl 3,4,6-tri-O-acetyl-2-deoxy-α/β-D-glucopyranoside (47 g) (from example 3) in acetic acid (40 ml) and acetic anhydride (110 ml) was added concentrated sulphuric acid (0.94 ml) at 0°. The reaction mixture was brought to room temperature and stirred. After 2 hours the reaction mixture was diluted with water (50 ml) and extracted into $CH_2Cl_2$ (3×150 ml). The organic phase was separated, washed with saturated $NaHCO_3$ solution $H_2O$ dried over $Na_2SO_4$ and concentrated to obtain 2-deoxy-1,3,4,6-tetra-O-acetyl-α/β-D-glucopyranoside as a crystalline compound. mp. 115–118° C. Quantity obtained 44.5 g (86%). $[\alpha]_D$+21.5° (c 1.0, $CHCl_3$). $^1H$ NMR (200 MHz, $CDCl_3$): δ 1.50–2.45 (m, 14H, H-2,2', 4×OCOCH$_3$), 3.85–5.40, (m, 5H, H-3,4,5,6,6'), 5.75–6.20 (m, 1H, H-1, α/β). To a heterogeneous mixture of 1,3,4,6-tetra-O-acetyl-2-deoxy-α/β-D-glucopyranoside (10 g) in water (100 ml) was added acetyl chloride (10 ml) and heated to 80° C. After 6 hours the reaction mixture was cooled to room temperature, neutralised with saturated aq. Ba(OH)$_2$, concentrated to half the volume and filtered on a Celite pad, Filtrate was concentrated on a rotary evaporator and dried over anhydrous $P_2O_5$ to obtain a residue which was dissolved in hot isopropyl alcohol and filtered on a pad of Celite to obtain a clear filtrate. The filtrate was concentrated to a residue, dissolved in hot isopropyl alcohol (50 ml), acetone (75 ml) and seeded with a few crystals of 2-deoxy-D-glucose. After 15–18 hours at 5° C. crystalline title product was filtered. Quantity obtained 3.21 g (64.9%) m.p. 148–149° C.

EXAMPLE 6

A heterogeneous mixture of 1,3,4,6-tetra-O-acetyl-2-deoxy-α/β-D-glucopyranoside (9 g) (from example 5), water (30 ml) and 11% aq. $H_2SO_4$ (0.3 ml) was stirred at 85° C. for 7 h to obtain a homogeneous solution. The reaction mixture was cooled, neutralised with aq. Ba(OH)$_2$ solution and filtered. The filtrate obtained was concentrated to half the volume and solids separated were filtered. To the filtrate was added activated carbon (1 g) and filtered. The filtrate was concentrated on a rotary evaporator and dried over $P_2O_5$ to obtain 2-deoxy-D-glucose that was crystallized from methyl alcohol (27 ml) and acetone (54 ml). Quantity obtained 2.4 g. mp. 146–149° C.,

EXAMPLE 7

A heterogeneous mixture of 1,3,4,tetra-O-acetyl-2-deoxy-α/β-D-glucopyranoside (25 g) (from example 5), $H_2O$ (250 ml), toluene (250 ml) and glacial acetic acid (1.25 ml) was heated to reflux for 10–12 hours, while it was connected to a Dean-Stark azeotropic distillation apparatus. An azeotropic mixture of acetic acid, toluene was collected to remove acetic acid and every one hour fresh toluene (50 ml) was introduced. After completion of the reaction, toluene was removed by distillation from the reaction mixture to obtain a residue that was dissolved in methanol, treated with charcoal and filtered. Be filtrate was separated, concentrated to a residue and crystallized from isopropyl alcohol and acetone to obtain 2-deoxy-D-glucose (7.33 g, 59%). mp. 148–151° C.

EXAMPLE 8

A heterogeneous mixture of 1,3,4,5-tetra-O-acetyl-2-deoxy-α/β-D-glucopyranoside (10 g) (tom example 5), $H_2O$ (200 ml) conc. HCl (0.3 ml) and glacial acetic acid (0.5 ml) was heated to 85° C. After 6 hours the reaction mixture was cooled to room temperature, neutralized with aq. Ba(OH)$_2$ and filtered on a pad of Celite. Filtrate was separated, treated with charcoal and filtered. The filtrate was concentrated to a residue and crystallized from MeOH, acetone to obtain the product. Quantity obtained 275 g. mp. 147–148° C.

EXAMPLE 9

A heterogeneous mixture of 1,3,4,5-tetra-O-acetyl-2-deoxy-α/β-D-glucopyranoside (10 g) (from example 3) water (100 ml) and conc. HCl (0.5 ml) was heated to 80° C. After 2–5 hours the reaction mixture was cooled to room temperature, neutralized with aq. Ba(OH)$_2$ and filtered on a pad of Celite. The filtrate was concentrated to a residue, dissolved in ethanol, treated with charcoal and filtered. The filtrate was concentrated to a solid residue and crystallized from methanol-acetone to obtain the title product. Quantity obtained 3.15 g mp. 148–151° C.,

EXAMPLE 10

A solution of methyl 2-deoxy-α/β-D-glucopyranoside (30 g) (from example 2) water (15 ml) and conc. HCl (1.5 ml) was heated to 80–85° C. After 3–5 hours the reaction mixture was cooled to room temperature, neutralize with aq. Ba(OH)$_2$ and filtered to remove insoluble salts. The filtrate was concentrated to a residue, crystallized from MeOH, acetone and hexane to obtain 2-deoxy-D-glucose (11.77 g) mp. 149–151° C.

EXAMPLE 11

A solution of methyl 2-deoxy-α/β-D-glucopyranoside (30 g) (form example 2) water (195 ml) and conc. $H_2SO_4$ (5.9 ml) was heated to 80° C. After 2–3 hours the reaction mixture was cooled, neutralized with aq. Ba(OH)$_2$ and filtered. The filtrate was separated, treated with charcoal and filtrate. The Filtrate was concentrated to a residue and crystallized from isopropyl alcohol to obtain the title product. Quantity obtained 5.2 g. mp. 152–154° C.

EXAMPLE 12

A mixture of methyl 2-deoxy-α/β-D-glucopyranoside (24 g) (from example 2) water (125 ml) and IR 120H+resin (7.5 ml) was heated to 90–95° C. for 2 h. The reaction mixture was cooled to room temperature, filtered and the resin was washed with water (20 ml). The filtrate was concentrated to residue and crystallized from ethanol to obtain 2-deoxy-D-glucose (8.8 g), mp. 150–152° C.

The main advantages of the present invention are:

1). It does not involve the use of toxic mercaptans like ethane thiol.
2). This process does not involve reaction of D-glucal with mineral acid, thereby avoiding the formation of Ferrier by-products.

We claim:

1. A process for the synthesis of 2-deoxy-D-glucose comprising:

the haloalkoxylation of R-D-Glucal wherein R is selected from H and 3, 4, 6-tri-O-benzyl, to obtain alkyl 2-deoxy-2-halo-R-α/β-D-gluco/mannopyranoside, converting alkyl 2-deoxy-2-halo-R-α/β-D-gluco/mannopyranoside by reduction to alkyl 2-deoxy-α/β-D-glucopyranoside, and hydrolysing alkyl 2-deoxy-α/β-glucopyranoside to 2-deoxy-D-glucose.

2. A process as claimed in claim 1 wherein alkyl 2-deoxy-α/β-D-glucopyranoside is obtained by (a) haloalkoxylating 3,4,6,-tri-O-benzyl-D-glucal to alkyl 2-deoxy-2-halo-3,4,6-tri-O-benzyl-α/β-D-gluco/mannopyranoside;

(b) subjecting alkyl 2-deoxy-2-halo-3,4,6-tri-O-benzyl-α/β-D-gluco/mannopyranoside to reduct dehalogenation and debenzylation to obtain alkyl 2-deoxy-α/β-glucopyranoside.

3. A process as claimed in claim 2 wherein in step (a) haloalkoxylation of 3,4,6-tri-O-benzyl-D-glucal is carried out by reaction with a haloalkoxylating agent selected from a N-halosuccinimide and a N-haloacetamide, and alcohol.

4. A process as claimed in claim 3 wherein the N-halosuccinimide is selected from N-chloro- and N-bromosuccinimide.

5. A process as claimed in claim 3 wherein haloalkoxylation is carried out at a temperature in the range of 0° C.–30° C.

6. A process as claimed in claim 5 wherein the temperature is in the range of 5–10° C.

7. A process as claimed in claim 3 wherein the alcohol is selected from the group consisting of methanol, ethanol and isopropyl alcohol.

8. A process as claimed in claim 3 wherein the alcohol comprises stoichiometric amounts of alcohol contained in ethylene dichloride or dichloromethane.

9. A process as claimed in claim 3 wherein the N-haloacetamide comprises N-bromoacetamide.

10. A process as claimed in claim 2 wherein step (b) is carried out in the presence of an alcohol selected from ethanol and isopropyl alcohol or water and in the presence of a scavenger selected from the group consisting of triethyl amine, $Na_2CO_3$, disopropyl amine and hexylamine.

11. A process as claimed in claim 1 wherein alkyl 2-deoxy-α/β-D-glucopyranoside is obtained by (a) haloalkoxylating D-glucal to alkyl 2-deoxy-2-halo-α/β-D-gluco/mannopyranoside;

(b) subjecting alkyl 2-deoxy-2-halo-α/β-D-gluco/mannopyranoside to reduct dehalogenation and hydrogenation to obtain alky 2-deoxy-α/β-D-glucopyranoside.

12. A process as claimed in claim 11 wherein haloalkoxylation of D-glucal in step (a) comprises reaction with an haloalkoxylating agent selected from N-halosuccinimide and N-haloacetamide, and an alcohol.

13. A process as claimed in claim 12 wherein the N-halosuccinimide is selected from N-chloro- and N-bromosuccinimide.

14. A process as claimed in claim 11 wherein the haloalkoxylation is carried out in the presence of a solvent selected from the group consisting of EtOH, iPrOH, N,N-dimethyl formamide and stoichiometric amounts of alcohol.

15. A process as claimed in claim 11 wherein the reductive dehalogenation is carried out in the presence of a solvent selected from the group consisting of water, MeOH, EtOH and iPrOH, and with Pd/C 10% catalyst.

16. A process as claimed in claim 11 wherein the haloalkoxylation is bromomethoxylation, N-halosuccinimide is N-bromosuccinimide, alcohol is methanol and alkyl 2-deoxy-2-halo-α/β-D-gluco/mannopyranoside is methyl 2-bromo-2-deoxy-α/β-D-gluco/mannopyranoside.

17. A process as claimed in claim 11 wherein the hydrogenation is carried out at a pressure in the range of about 40–120 psi and in the presence of Raney-nickel catalyst.

18. A process as claimed in claim 17 wherein said Raney nickel catalyst is used as a methanolic slurry.

19. A process as claimed in claim 11 wherein reductive dehalogenation is reductive debromination and said methyl 2-deoxy-2-halo-α/β-D-gluco-/mannopyranoside is methyl 2-bromo-2-deoxy-α/β-D-gluco-/mannopyranoside and wherein the methyl 2-bromo-2 deoxy-α/β-D-gluco/mannopyranoside is converted to methyl 2-deoxy-α/β-D-glucopyranoside by hydrogenation using triethylamine at a pressure in the range of 40–120 psi in the presence of a Raney nickel catalyst.

20. A process as claimed in claim 1 wherein the alkyl 2-deoxy-α/β-D-glucopyranoside is directly hydrolysed to 2-deoxy-D-glucose by a hydrolysing agent selected from the group consisting of $CF_3CO_2H$, HCl and HOAc.

21. A process as claimed in claim 1 wherein hydrolysis of alkyl 2-deoxy-α/β-D-glucopyranoside to 2-deoxy-D-glucose is done at a temperature in the range of 20–90° C.

22. A process as claimed in claim 1 wherein the alkyl 2-deoxy-α/β-D-glucopyranoside is first acetylated to alkyl 2-deoxy-3,4,6-tri-O-acetyl-α/β-D glucopyranoside which is then converted to 2-deoxy-1,3,4,6-tetra-O-acetyl-α/β-D-glucopyranoside which is then hydrolysed to 2-deoxy-D-glucose.

23. A process is claimed in claim 22 wherein the hydrolysis of 2-deoxy-1,3,4,6-tetra-O-acetyl-α/β-D-glucopyranoside comprises acid catalysed hydrolysis.

24. A process as claimed in claim 23 wherein the acid catalysed hydrolysis is carried out using a hydrolysing agent selected from the group consisting of aqueous acetyl bromide, aqueous acetyl chloride and aqueous acetic acid.

25. A process as claimed in claim 22 wherein the hydrolysis of 2-deoxy- 1,3,4,6-tetra-O-acetyl-α/β-D-glucopyranoside comprises base catalysed hydrolysis.

26. A process as claimed in claim 25 wherein the base catalysed hydrolysis is carried out using a hydrolysing agent selected from the group consisting of NaOMe, NaOi-Pr, LiOMe, NaOBu, $NH_3$/MeOH, $Bu_2SnO$/MeOh.

27. A process as claimed in claim 1 wherein the alkyl is selected from the group consisting of methyl, ethyl and isopropyl.

* * * * *